United States Patent [19]

Patel et al.

[11] Patent Number: 5,776,912
[45] Date of Patent: *Jul. 7, 1998

[54] LIPOPHILIC OLIGOSACCHARIDE ANTIBIOTIC COMPOSITIONS

[75] Inventors: Mahesh G. Patel, Verona; Vincent P. Gullo, Liberty Corner; Roberta S. Hare, Gillette, all of N.J.; David Loebenberg, Monsey, N.Y.; Heewon Y. Kwon, Warren; George H. Miller, Montville, both of N.J.

[73] Assignee: Schering Corporation, Kenilworth, N.J.

[*] Notice: The term of this patent shall not extend beyond the expiration date of Pat. No. 5,624,914.

[21] Appl. No.: 770,470

[22] Filed: Dec. 20, 1996

[51] Int. Cl.⁶ ................................................. A61K 31/70
[52] U.S. Cl. ........................... 514/54; 536/16.8; 536/123.1
[58] Field of Search ...................... 514/54, 58; 536/16.8, 536/103, 123.1

[56] References Cited

U.S. PATENT DOCUMENTS 5,624,914  4/1997  Patel et al. ................................. 514/54

Primary Examiner—Elli Peselev
Attorney, Agent, or Firm—Thomas D. Hoffman

[57] ABSTRACT

An aqueous pharmaceutical composition comprising a lipophilic oligosaccharide antibiotic salt, e.g., the N-methylglucamine salt of the everninomicin-type antibiotic of Formula III together with a binding agent such as human serum albumin or recombinant human albumin and a tonicity agent such as mannitol, is disclosed.

27 Claims, 1 Drawing Sheet

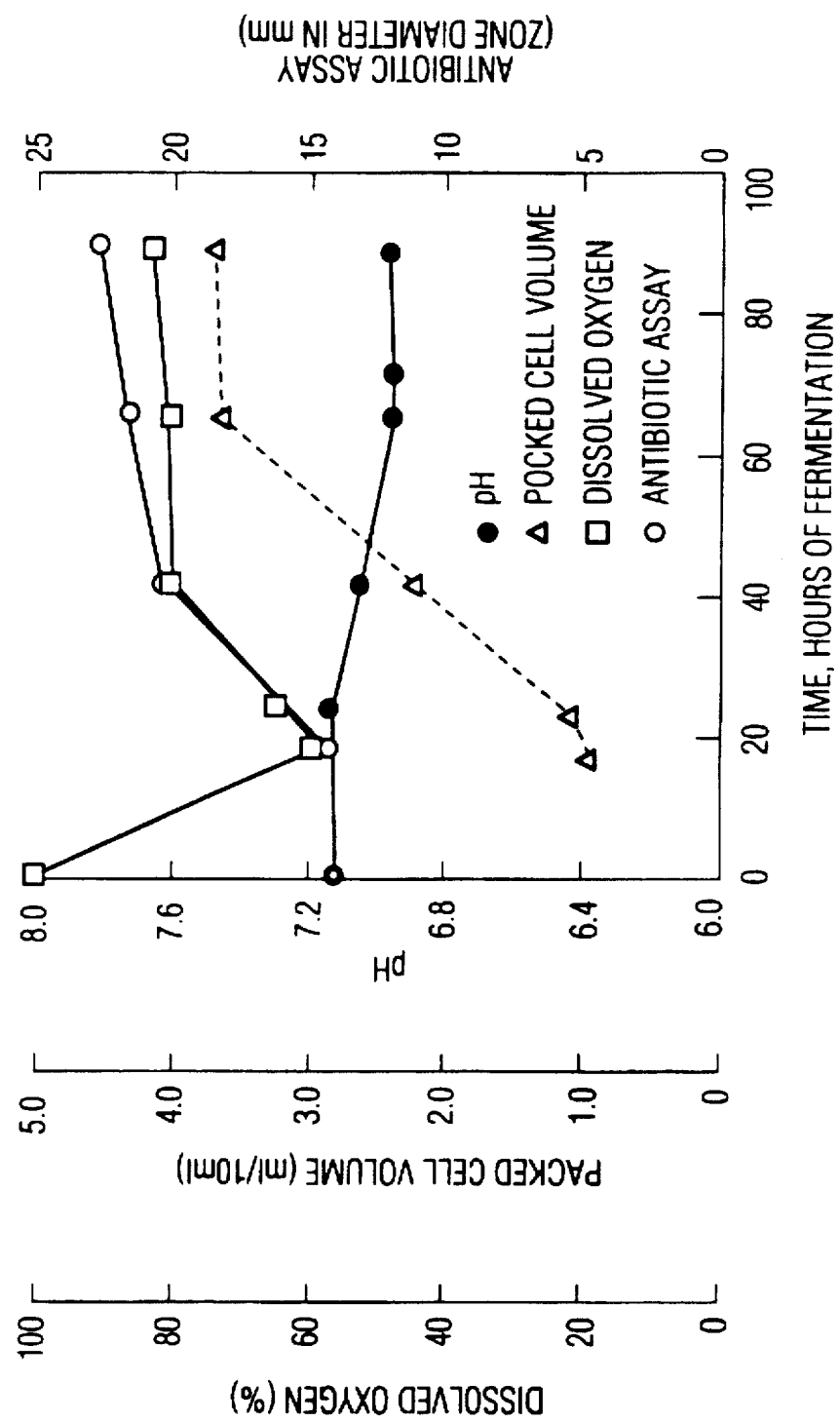
FIGURE

LIPOPHILIC OLIGOSACCHARIDE ANTIBIOTIC COMPOSITIONS

BACKGROUND OF THE INVENTION

This invention relates to novel compositions of matter comprising a lipophilic oligosaccharide antibiotic salt together with a binding agent and to pharmaceutical formulations containing such compositions of matter and to methods of making and using such pharmaceutical compositions to treat and/or prevent microbial infections in animals especially mammals such as human beings.

Lipophilic oligosaccharide antibiotics including, for example, everninomicins, curamycins, avilamycins and flambamycins are members of the orthosomycin family of antibiotics which contain at least one acidic phenolic hydrogen, and two orthoester linkages associated with carbohydrate residues. See for example, A. K. Ganguly in "Kirk-Othmer, Encyclopedia of Chemical Technology", (1978), vol. 2, pp. 205-209, Third Edition, John Wiley and Sons and W. D. Ollis, et al., *Tetrahedron* (1979), vol. 35, pp. 105-127. These lipophilic oligosaccharide antibiotics exhibit broad spectrum biological activity against gram positive and some gram negative bacteria in various in vitro assays, and in vivo activity in animal models such as mice. It has been observed that injection of these lipophilic oligosaccharide antibiotics cause an adverse reaction syndrome. The term "adverse reaction syndrome" as used herein means symptoms of the following type observed in animals such as mice upon parenteral administration of lipophilic oligosaccharide antibiotics: incoordination, ataxia, lateral recumbency, urination, hind leg rigidity, labored breathing, and arrest.

International Publication No. WO 93/07904 discloses pharmaceutically acceptable compositions containing an amount of a pharmaceutically acceptable non-ionic surfactant and lipophilic oligosaccharide antibiotics, e.g., the everninomicin antibiotic of formula III with at least a stoichiometric amount of a base and an amount of hydroxypropyl-α—,—β— or —γ— cyclodextrins sufficient to achieve efficacious delivery of the oligosaccharide antibiotic to the serum of an animal while simultaneously avoiding adverse reaction syndrome.

Cyclodextrins provide efficacious delivery of the oligosaccharides antibiotic to the serum but cyclodextrins are expensive materials and not a GRAS (generally regarded as safe) material. There is a need for alternative pharmaceutically acceptable compositions of liphophilic oligosaccharide antibiotic salts which are solubilized by agents other than cyclodextrins.

Various strains of bacteria such as gram-positive cocci, e.g., streptococci and enterococci as well as methicillin-resistant and methicillin-susceptible staphylococci have become, and continue to become resistant to commercially available antibiotics, e.g., vancomycin. Such sensitive and resistant strains of gram-positive bacteria are an important cause of hospital-acquired and community-acquired infections. Such bacteria are recognized as significant pathogens that cause life-threatening illnesses. The commercially available antibiotics such as methicillin, macrolides, penicillins, quinolones as well as vancomycin have limitations including the aforesaid resistance and sensivity to gram-positive bacteria.

Thus, there is a need for pharmaceutically acceptable compositions for treating bacterial infections including methicillin-resistant and methicillin-susceptible staphylococci and vancomycin-resistant bacteria. There is also a need for improved pharmaceutically acceptable compositions containing a lipophilic oligosaccharide antibiotic active against a broad range of susceptible gram-positive and gran-negative bacterial infections, especially pharmaceutical compositions adapted for parenteral use which avoid occurrence of the adverse reaction syndrome.

BRIEF SUMMARY OF THE INVENTION

Surprisingly, we have discovered a means by which lipophilic oligosaccharide antibiotics having good antibacterial activity against susceptible gram-positive and/or gram-negative bacterial infections may be delivered to animals, especially mammals such as man, afflicted with susceptible gram-positive or gram-negative bacterial infections, to provide effective treatment and/or prevention thereof while simultaneously avoiding occurrence of the adverse reaction syndrome. This means comprises combining a lipophilic oligosaccharide antibiotic with at least about a stoichiometric amount of a specified base and an amount of a binding agent such as natural human serum albumin ("WHSA") or recombinant human albumin ("rHA") sufficient to achieve efficacious delivery of the lipophilic oligosaccharide antibiotic to the serum of an animal while simultaneously avoiding adverse reaction syndrome.

The present invention provides a composition of matter comprising:

(a) a lipophilic oligosaccharide antibiotic represented by Formula I;

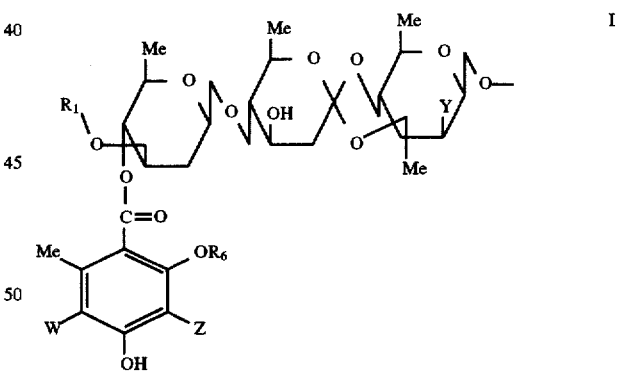

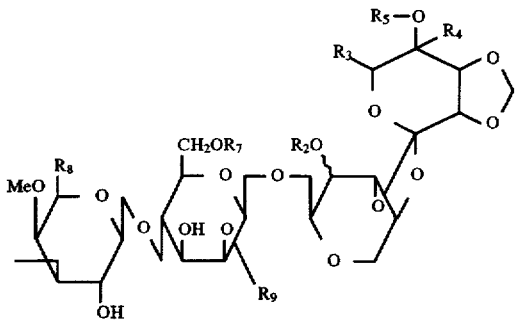

wherein

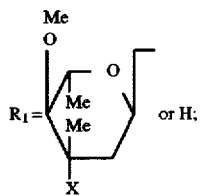

X is one of $NO_2$, NO, $NH_2$, $NHCOCH_3$, NHOH, $NH(C_2H_5)$, $N(C_2H_5)_2$, OH or H;

(c) an amount of a binding agent sufficient to achieve efficacious delivery of said lipophilic oligosaccharide antibiotic to the serum of an animal while simultaneously avoiding adverse reaction syndrome; and (d) 0 percent by weight (basis, the total weight of said composition) up to an iso-osmotic amount of a pharmaceutically acceptable tonicity agent.

The present invention also provides a composition of matter comprising (a) a compound represented by the Formula II

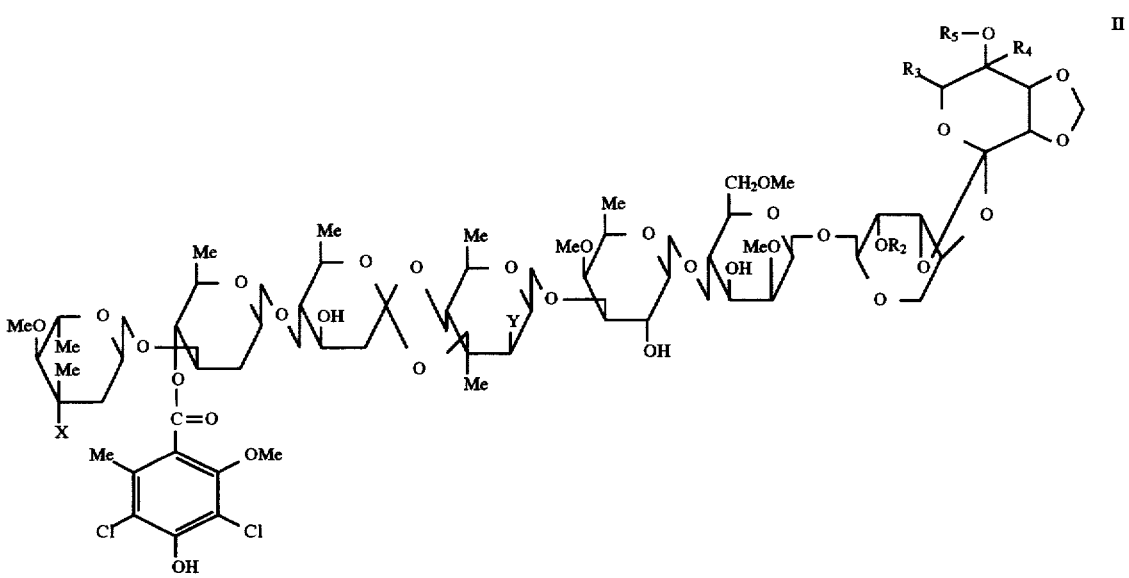

$R_2$ is one of $CH_3$, $COCH(CH_3)_2$, $COCH_3$, $CO(CH_2)_3CH_3$, $COCH_2CH_3$ or H;

$R_3$ is one of $CH_3$ or H;

$R_4$ is one of $COCH_3$, $CH(OCH_3)(CH_3)$, $CH(OH)CH_3$, CHO, or H;

$R_5$ is one of

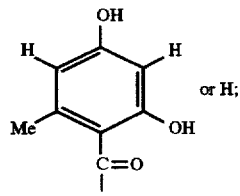

$R_6$ is $CH_3$ or H;
$R_7$ is $CH_3$ or H;
$R_8$ is $CH_3$, $CH_2OH$ or H
$R_9$ is $CH_3$ or H;
Y is OH, $CH_3$, or H;
W is Cl or H; and
Z is Cl or H.

(b) at least about a stoichiometric amount of a base capable of forming a pharmaceutically acceptable salt with a lipophilic oligosaccharide antibiotic of Formula I;

wherein X is one of $NO_2$, NO, NHOH, $NH_2$, $NHCOCH_3$, $NHC_2H_5$, $N(C_2H_5)_2$, OH or H
Y is OH or H
$R_2$ is H or $CH_3$
$R_3$ is H
$R_4$ is H or $CH(OCH_3)(CH_3)$
and

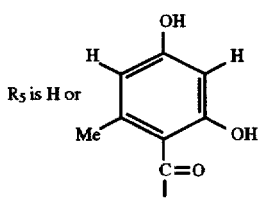

$R_5$ is H or (b) at least about a stoichiometric amount of a base capable of forming a pharmaceutically acceptable salt with a lipophilic oligosaccharide antibiotic of Formula II;

(c) an amount of a binding agent sufficient to achieve efficacious delivery of said lipophilic oligosaccharide antibiotic to the serum of an animal while simultaneously avoiding occurrence of adverse reaction syndrome; and (d) 0 percent by weight (basis, total weight of said composition) up to an iso-osmotic amount of a pharmaceutically acceptable tonicity agent.

The present invention further provides a composition of matter comprising (a) the antibiotic compound represented by Formula III parenteral injection of a lipophilic oligosaccharide antibiotic represented by Formula I, II or III while simultaneously delivering an antiinfective amount of said antibiotic to an

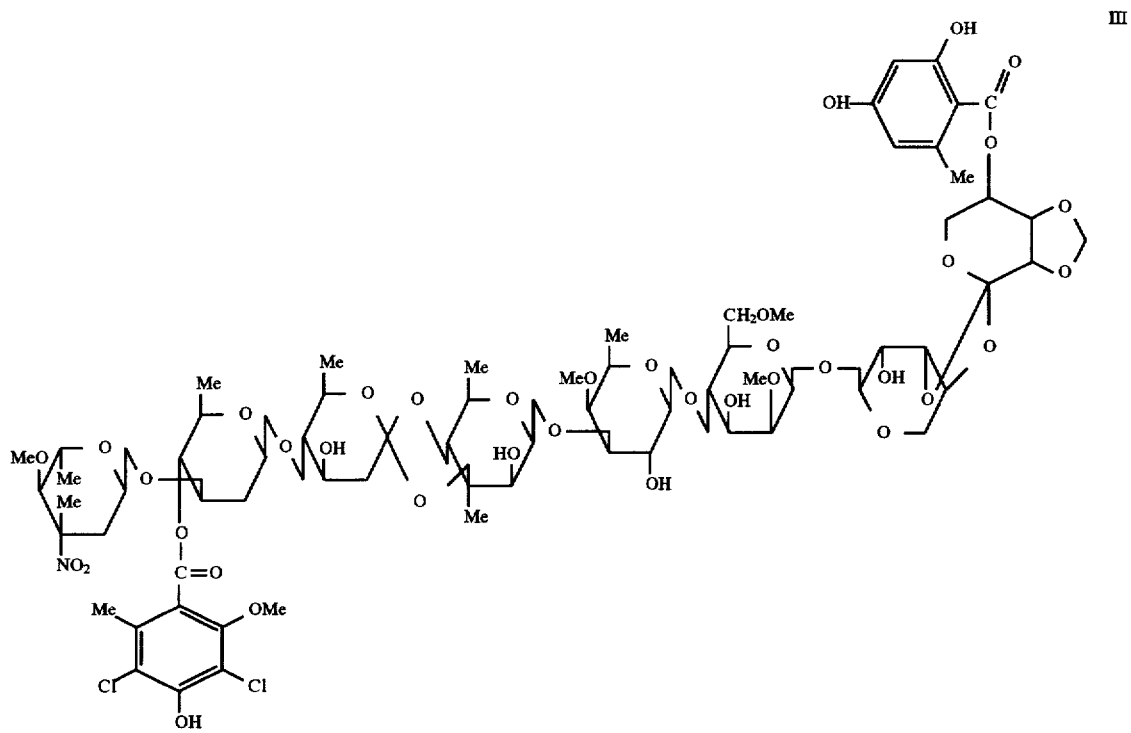

(b) at least about two equivalents of a base (per mole of the compound of Formula III) capable of forming a pharmaceutically acceptable salt of the compound of Formula III (c) an amount of binding agent sufficient to achieve efficacious delivery of said lipophilic oligosaccharide antibiotic to the serum of an animal while simultaneously avoiding occurrence of adverse reaction syndrome; and (d) 0 percent by weight (basis, said antibiotic of Formula III) up to an iso-osmotic amount of a pharmaceutically acceptable tonicity agent.

A preferred composition of matter of this invention contains the following: (a) the compound represented by Formula II, (b) N-methylglucamine, (c) recombinant human albumin ("rHA"), and (d) an iso-osmotic amount of mannitol; wherein the molar ratio of (a):(b):(c) is 1: about 3–3.5: about 0.018–0.030 and the amount of the mannitol the preferred tonicity agent, is about 35 to 45% weight percent (basis total composition).

Pharmaceutical compositions formed by admixing a composition of matter comprising a compound represented by Formulas I, II or III and at least about a stoichiometric amount of a base capable of forming a pharmaceutically acceptable salt thereof and an amount of a binding agent with a pharmaceutically acceptable tonicity agent and pharmaceutically acceptable carriers as well as methods of using such pharmaceutical compositions for treating or preventing susceptible gram positive and gram negative bacterial infections in animals, especially mammals in need of such treating or preventing are also provided.

As a preferred form of the invention, the aforesaid pharmaceutical compositions are particularly applicable to parenteral administration, especially in vivo administration to human beings by the intravenous (IV) route.

The present invention also provides a method of preventing adverse reaction syndrome in animals following animal, which method comprises parenterally administering to said animal an amount of a composition of matter of this invention sufficient for such purpose together with a pharmaceutically acceptable carrier.

BRIEF DESCRIPTION OF THE FIGURES

FIG. 1 graphically illustrates the progression, with time, of a typical fermentation of *Micromonospora carbonacea*. var. africana, NRRL 15099, ATCC 39149.

DETAILED DESCRIPTION OF THE INVENTION AND OF THE PREFERRED EMBODIMENTS

Lipophilic oligosaccharide antibiotics, for example eveminomicin antibiotics, exhibit useful in vitro antibacterial activity but do not readily form complete aqueous solutions suitable for safe and effective in vivo administration (i.e. without occurrence of adverse reaction syndrome). Moreover, salts of these antibiotics formed by admixing at least about a stoichiometric amount of a base useful in this invention, e.g. the base, N-methylglucamine ("NMG") do not form complete aqueous solutions, at useful pH values. When said salts were added to water at useful concentrations of salt, we observed that only colloidal dispersions were formed. These colloidal dispersions tended to aggregate, and eventually gelled, especially in the presence of absorbed carbon dioxide and when the pH of such colloidal dispersions was less than about 9.3. We observed that complete aqueous solutions were formed by increasing the molar ratio of NMG to the compound of Formula III from 2:1 or 3:1 up to 12:1, but that the solution so formed with the 12:1 molar ratio had an undesirably high pH, was highly buffered and was irritating. Thus, we observed that parenteral injection into rats or higher primates, such as monkeys, of an aqueous formulation containing 12 moles of NMG per one mole of the compound of Formula III did not result in adverse reaction syndrome (presumably caused by gelling and precipitation of the compound of Formula III). The formulation, produced irritation upon injection, which irritation is presumably caused by the large amount of NMG base and resulting high pH at the injection site. However, parenteral administration of a composition containing 3 or 5 moles of NMG per mole of the compound of Formula III gave rise to adverse reaction syndrome. Surprisingly, we have found that a composition of matter comprising a lipophilic oligosaccharide antibiotic compound of Formula III, a specified amount of a specific base, e.g., NMG and a specified binding agent, e.g., human serum albumin in specified amounts provides, when admixed with pharmaceutically acceptable carriers, especially sterile water for injection, a formulation which may be used safely and effectively for in vivo administration. Surprisingly, we have found that when 1 mole of a lipophilic oligosaccharide antibiotic, e.g., the compound of Formula III was admixed with 3 moles of a suitable base, e.g., NMG, in water and with 0.027 moles of human serum albumin, a clear aqueous solution of the complex was formed and the parenteral injection of such complexes into mice did not cause adverse reaction syndrome even at high doses, i.e., 400 mg of such complex per kg of body weight. See Table 1

As will be evident from the in vivo results summarized in Table 1 parenteral injections of the aqueous dispersions of salts, e.g., the NMG salt of the eveminomicin-type antibiotic of Formula III into mice and rats gave rise to the adverse reaction syndrome. When the aqueous solutions of one of the compositions of matter of this invention such as one containing a specified binding agent, e.g., human serum albumin with the NMG eveminomicin-type antibiotic of Formula III salts were injected into the animals the occurrence of adverse reaction syndrome was wholly avoided.

Table 2 shows that adverse reaction syndrome can be reduced or completely avoided by parenteral injection into mice of clear aqueous solutions of NMG salts of the eveminomicin-type antibiotic of Formula III with the specified binding agent, human serum albumin, of this invention.

Table 3 illustrates that increasing the molar ratio of base to the eveminomicin-type antibiotics of Formula III from 2:1 to 9:1 wholly eliminates the occurrence of adverse reaction syndrome at all concentrations tested upon parenteral injection into mice.

COMPARATIVE EXAMPLE

TABLE 1

COMPARATIVE EXAMPLE
THE OCCURRENCE OF ADVERSE REACTION SYNDROME AFTER ADMINISTRATION OF AQUEOUS FORMULATIONS OF ONE MOLE OF THE COMPOUND OF FORMULA III: AND OF 3 MOLES NMG WITH AND WITHOUT HSA[1]

| Mice (Concentration of III Injected: 80 mg/mL) | % Adverse Reaction Syndrome[2] at the following DOSES (MPK[3]) | | | | |
|---|---|---|---|---|---|
| | 160[3] | 200[3] | 320[3] | 400[3] | 520[3] |
| III[4]: 3 NMG | 100 | 100 | — | — | — |
| III: 3 NMG: 0.027 HSA[5] | — | 0 | 0 | 0 | 40 |

| Rats (Concentration of III Injected: 80 mg/mL) | % Adverse Reaction Syndrome at the following DOSES (MPK[6]) | | | | | |
|---|---|---|---|---|---|---|
| | 60[6] | 80[6] | 100[6] | 160[6] | 200[6] | 300[6] |
| III: 3 NMG | 60 | 100 | 100 | 100 | 100 | — |
| III: 3 NMG: 0.027 HSA[5] | — | — | 0 | 0 | 0 | 40 |

Footnotes to Table 1
[1] Human serum albumin
[2] Adverse Reaction Syndrome symptoms were observed in the animals within 2 minutes after IV injection. (single dose)
[3] MPK is mg of drug per kg of body weight of the mice (groups of 10, CF1, average weight 20 g, Harlan Sprague - Dawley fasted 18 hours.)
[4] III is the eveminomicin-type antibiotic compound represented by Formula III.
[5] 0.027 moles HSA is equivalent to 9% w/v HSA based on an 80 mg/ml solution of the compound of Formula III.
[6] MPK is mg of drug per kg of body weight of the rats (groups of 5, average weight 180–200 g, Charles River, fasted 18 hours)

TABLE 2

Adverse Reaction Syndrome (ARS)[1] Upon Administration of Aqueous Formulations of the Compound of Formula III and NMG in a molar ratio of 1:3 and Containing Various Weight Percents of HSA

| Drug of Formula III Injected HSA[3] | | % ARS at the following doses (MPK[2]) of Drug of Formula III (80 mg/ml) in Mice | | | | | | | | | | |
|---|---|---|---|---|---|---|---|---|---|---|---|---|
| | concentration[4] | 40 | 60 | 80 | 100 | 160 | 200 | 400 | 500 | 600 | 700 | 800 |
| III:3NMG | 0 | 0 | 10 | 50 | 100 | 100 | 100 | — | — | — | — | — |
| III:3NMG | 2% | — | 0 | 30 | 50 | 100 | 100 | 100 | — | — | — | 100 |
| III:3NMG | 4% | — | — | — | 0 | — | 30 | 100 | — | — | — | — |
| III:3NMG | 6% | — | — | — | — | — | — | 0 | 50 | 100 | — | — |
| III:3NMG | 8% | — | — | — | — | — | — | 0 | 0 | 0 | 70 | 100 |
| III:3NMG | 10% | — | 0 | — | — | — | — | 0 | 0 | 10 | 50 | 70 |

Footnotes to Table 2
[1] Adverse Reaction Syndrome Symptoms observed in the mice (groups of 5 to 10, CF-1, average weight 20 g, Harlan Sprague Dawley fasted 18 hours) within 2 minutes after IV (single dose) injection
[2] MPK is mg of drug substance of Formula III per kg of animal body weight.
[3] HSA is human serum albumin available from Armour Pharmaceutical Div., Rhone-Poulenc Rorer, 500 Arcola Rd. Collegeville, PA 19426
[4] Percent (W/V) based on the Aqueous formulation containg 80 mg/mL of the compound of formula III

TABLE 3

Effect of Concentration of
Lipophilic Oligosaccharide Antibiotic NMG Salt and
Molar ratio of NMG to Antibiotic upon
Adverse Reaction Syndrome[1] in Mice

| Drug of Formula III | % ARS[1] at the following doses (MPK[2]): | | | | |
|---|---|---|---|---|---|
| (Drug Concentration) | 50 | 100 | 200 | 300 | 400 |
| III[3]: 2 NMG (10 mg/ml) | 0 | 10 | 50 | — | — |
| III: 2 NMG (20 mg/ml) | 0 | 20 | 100 | 100 | — |
| III: 2 NMG (50 mg/ml) | 70 | 100 | — | — | — |
| III: 3 NMG (20 mg/ml) | — | 0 | 0 | 0 | 20 |
| III: 3 NMG (40 mg/ml) | — | 0 | 0 | 15 | 40 |
| III: 3 NMG (80 mg/ml) | — | — | 100 | — | — |
| III: 5 NMG (20 mg/ml) | — | 0 | 0 | 0 | — |
| III: 5 NMG (50 mg/ml) | — | — | 0 | — | 40 |
| III: 9 NMG (20 mg/ml) | — | 0 | 0 | 0 | 0 |
| III: 9 NMG (40 mg/ml) | — | 0 | 0 | 0 | 0 |
| III: 9 NMG (80 mg/ml) | — | — | 0 | — | 0 |

Footnotes to Table 3
[1]Adverse Reaction Syndrome Symptoms observed in mice (groups of 5 to 10, CF-1, average weight 20 g, Harlan Sprague Dawley, fasted 18 hours) within 2 minutes after IV (single dose) injection
[2]MPK is mg of the drug of Formula III per kg of body weight.
[3]III is everninomicin-type antibiotic compound represented by Formula III.

TABLE 4

PD 50 Valves Showing Efficacy of Composition Containing the
Compound of Formula III Against Bacterial Infections[1] in CF1 Mice[2]

| Organism[3] | No. × 5 LD10 | CFU[6] Mouse | DRUGS[4] | | | |
|---|---|---|---|---|---|---|
| | | | A | B | C | D |
| S. aureus 85111205 | 10 | 6.3 × 10⁹ | 9 | 11 | 26 | — |
| S. aureus 78100502 | 20 | 2.2 × 10⁸ | 12 | 12 | 6 | — |
| E. faecalis 88032810 | 10 | 9.7 × 10⁸ | 21 | 16 | 10 | 115 |
| E. faecalis 91031103 Vancomycin resistant | 1.7 | 1.5 × 10⁹ | 60 | 60 | 100 | 49 |

Footnotes for Table 4
[1]Injections were by IP route
[2]CFI mice are Charles River CFI, ca 20 g while male mice
[3] a Staphylococcus aureus 85111203 and 78100502
  b Enterococcus faecalis 803280 (Perm., APH-(3')-III) and 91031103 (Vancomycin resistant)
[4]PD$_{50}$ Dosing routes for drugs: IV for A, B and C; SC for D in mg/Kg of body weight
Drug A is compound of formula III:NMG:HPβCD in the molar ratio of 1:3:5 with Polysorbate 80 and mannitol in sterile water for injection (SWFI)
Drug B is the compound of formula III:NMG:HSA in the molar ratio of 1:3:0.027 and mannitol in SWIFI
Drug C is Vancomycin HCl intravenous available from Eli Lilly Co., Indianapolis; conc 10 mg vancomycin in 1 ml of SWFI).
Drug D is Amikacin
[5]Multiple of one LD100 (lethal dose to kill 100% of animals) of organism given to mice. (Measure of severity of the infection.)
[6]Amount of organism administered to mice in Colony Forming Units ("CFU's").

Perhaps even more surprisingly, we observed that the Minimum inhibitory Concentrations ("MIC") in the in vitro models, and the 50% protective dose ("PD$_{50}$") values in an in vivo mouse protection model, of the composition of 0.027 human serum albumin in combination with one mole of the compound of Formula III and 3 moles of NMG (Drug B in Table 4) were essentially the same as the MICs and PD$_{50}$ values for the compound of Formula III and for those of the NMG salt of the compound of Formula III with HPβCD in said model (Drug A in Table 4). See Table 4 for PD50 values for the compositions of the compound of formula III including a preferred composition of the present invention (Drug B) compared to those for vancomycin (Drug C) and amikacin (drug D).

Thus, we have surprisingly discovered improved pharmaceutically acceptable compositions of matter containing a lipophilic oligosaccharide antibiotic salt and a binding agent such as HSA which allows effective delivery of such antibiotic to the serum of an animal such as a mammal especially a man afflicted with a bacterial infection susceptible to treatment by such lipophilic oligosaccharide antibiotics of Formulas I, II and III.

The term "binding agent" as used herein means a substance which has sufficient free highly lipophilic binding sites to achieve efficacious delivery of the lipophilic oligosaccharide antibiotics of formulas I, II and III to the serum of an animal while simultaneously avoiding occurrence of adverse reaction syndrome. Typically suitable binding agents include any protein with highly lipophilic binding sites as evidenced by its effective binding with fatty acids. Such proteins include natural human serum albumin ("HSA") and recombinant human albumin ("rHA"). HSA is produced as a product from fractions of collected blood. Human serum albumin is available from Armour Pharmaceutical Div., Rhone-Poulenc. Rorer, 500 Arcola Rd., Collegeville, Pa. 19426 and Fluka Chemika-BioChemika, Industriestrasse 25, CH-9470 Buchs, Switzerland. rHA is prepared by use of recombinant techniques such as described in EP 0 683 233 published 22 Nov. 1995 and is commercially available from Delta Biotechnology Ltd., NottinghamNG71 FD, Great Britain. Other binding agents include deoxycholic acid and salts thereof, for example, sodium deoxycholate which is available from Sigma Chemicals Co., P.O. Box 14508, St. Louis, Mo. 63178.

The moles of binding agent per mole of the compound of formula I, II or III varies from about 0.006 to about 0.03. If the binding agent is substantially free of impurities (i.e., contains<1–5%) such as fatty acids bound to the binding site of the agent, only about 0.006 moles (per mole of compound of formula I, II or III) of such purified binding agent would be needed to achieve effective delivery of the compounds of formula I, II of III to the serum of the mammals. Amounts of binding agent above about 0.03 moles per mole of compound of formulas I, II or III have no further beneficial effect. The preferred binding agent is rHA which is readily available free of impurities such as fatty acids binding to it; about 0.006 moles of rHA (2% w/v based on 80 mg/ml of the compound of formula III) is needed to effectively transfer the compound of formula I, II or III to the serum of a mammal.

The term "tonicity agent" as used herein means an agent which allows the pharmaceutical compositions of the present invention to have an osmotic pressure compatible with human serum. Typically suitable tonicity agents, which may be present in the preferred pharmaceutical compositions of the present invention, include mannitol, sodium chloride, glycine and dextrose. The prefered tonicity agent (when one is used,) is mannitol but any pharmaceutically acceptable tonicity agent would also be acceptable.

The term "iso-osmotic" as used herein in reference to the amount of tonicity agent means the amount of the tonicity agent sufficient to make the pharmaceutical compositions of the present invention upon administration to a mammal iso-osmotic with the plasma of such a mammal. The iso-osmotic amount of tonicity agent varies with the tonicity agent used and may conveniently be measured in accordance with the procedures described in "Remington's Pharmaceutical Sciences" A. R. Gennaro, ed, 1990, 18th Edition, Mack Publishing Co., Easton, Pa., Chapter 79 entitled "Tonicity, Osmoticity, Osmolality and Osmolarity", pages 1481–1498 at 1488–1491. The iso-osmotic amount of mannitol, the preferred tonicity agent, is preferably about 35 to 45% by weight basis total weight of all ingredients in the composition.

The bases found suitable for use in the present invention are those which form pharmaceutically acceptable salts of the lipophilic oligosaccharide antibiotics of Formulas I, II or III and include suitable organic and inorganic bases. Suitable organic bases include primary, secondary and tertiary alkyl amines, alkanolamines, aromatic amines, alkylaromatic amines and cyclic amines. Exemplary organic amines include the pharmaceutically acceptable bases selected form chloroprocaine, procaine, piperazine, glucamine, N-methylglucamine, N,N-dimethyl glucamine ethylenediamine, diethanolamine, diisopropylamine, diethylamine, N-benzyl-2-phenylethylamine, N-N'dibenzylethylenediamine, choline, clemizole, tris (hydroxymethyl)aminomethane, or D-glucosamine. The preferred organic bases include N-methyl glucamine ("NMG"), diethanolamine, and tris(hydroxymethyl) aminomethane ("TRISH"). Use of NMG in this invention is more preferred. The suitable inorganic bases include alkali metal hydroxides such as sodium hydroxide. The bases found useful in the preparation of compositions of matter of the present invention produce aqueous solutions having a pH of at least about 9.3. Lysine forms aqueous solutions having a pH of less than 9.3 and thus lysine is not a suitable base for the present invention. Divalent metal hydroxides such as the alkaline earth hydroxides, calcium hydroxide and barium hydroxide did not form aqueous solutions of the lipophilic oliogosaccharide antibiotics of Formulas I, II or III in the presence of a binding agent having a pH of at least about 9.3 and were unacceptable as bases for use in the present invention.

The term "at least about a stoichiometric amount" as used herein in reference to the bases useful in this invention means the amount of base needed to substantially completely react with (i.e. result in more than 99% complete reaction) the acidic phenolic hydrogens of the lipophilic oligosaccharides antibiotics of Formulas I, II, III having one or two or three phenolic hydrogens. For the compounds of Formulas I and II wherein $R_5$=H, there is only one phenolic acidic hydrogen per molecule and the stoichiometric amount of the pharmaceutically acceptable bases of this invention is at least about one mole of such base up to 12 moles of such bases. For the compounds represented by Formula I and II wherein

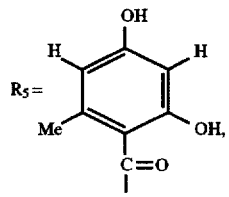

and for the compounds of Formula III there are three acidic phenolic hydrogens per mole of such compounds, the stoichiometric amount of base required to completely react with the three acidic phenolic hydrogens is at least one up to about 12 moles of the pharmaceutically acceptable bases useful in this invention.

For the preferred lipophilic oligosaccharide antibiotics of Formulas I, and II

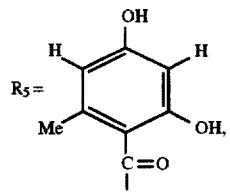

wherein and those of Formula III, it is preferred to use about one to 6 moles, and it is more preferred to use about 2.0 to 3.5 moles and most preferred to use about 2 to about 3 moles of a pharmaceutically acceptable base such as NMG to maintain the pH of an aqueous solution thereof at a value of about 9.3 as opposed to solutions having a higher pH, and which solutions were highly buffered when 6–12 moles of NMG were used.

The term "lipophilic oligosaccharide antibiotic" as used herein means selected lipophilic members of the orthosomycin family of antibiotics, more particularly flambamycin, the eveminomicins, eveminomicin-type antibiotics, curamycin and the avilamycin A-N antibiotics.

Flambamycin, a lipophilic oligosaccharide antibiotic produced by Streptomyces hygroscopicus DS 23230, whose structural Formula is that of Formula I wherein $R_1$=$R_5$=H, Y=OH, $R_2$=COCH(CH$_3$)$_2$, $R_3$=$R_6$=$R_7$=$R_8$=Rg=CH$_3$, $R_4$=COCH$_3$ and W=Z=Cl is disclosed by W. D. Ollis in Tetrahedron, (1979), 35, 105–127.

Curamycin A is a flambamycin antibiotic (having a structural Formula represented by Formula I wherein $R_1$, $R_3$, $R_4$, $R_5$, $R_6$, $R_7$, $R_8$, $R_9$, W and Z are the same as for flambamycin except $R_2$=COCH$_3$ and Y=H. See O. L. Galamarine et al. Tetrahedron (1961), 15, 76 and V., Deulofer et al., Anales de Quimica (1972), 68, 789.

Avilamycin A-N antibiotics are lipophilic oligosaccharide antibiotics isolated from an antibiotic complex produced by cultures of the organism Streptomyces viridochromogenes, NRRL 2860. See J. L. Mertz et al. The Journal of Antibiotics (July 1986) vol. 39 (No. 7) 877–887. The structural Formulas for the avilamycin A-N antibiotics are represented by Formula I wherein, $R_1$=$R_5$=H, Y=H, $R_2$=COCH(CH$_3$)$_2$, COCH$_3$, CO(CH$_2$)$_3$CH$_3$, COCH$_2$CH$_3$ or H, $R_3$=CH$_3$, $R_4$=COCH$_3$, CH(OH)CH$_3$ or CHO and $R_6$=CH$_3$ or H; $R_7$=CH$_3$ or H; $R_8$=CH$_3$, CH$_2$OH or H; $R_9$=CH$_3$ or H and W=H or Cl and Z=Cl.

The eveminomicin antibiotics useful in this invention include the eveminomicins B, C and D isolated from the antibiotic complex produced by the organism, *Micromonospora carbonacea* var. carbonacea NRRL 2972 and a variety thereof *M. carbonacea* var. aurantiaca NRRL 2997 as described in U.S. Pat. No. 3,499,078. The eveminomicin derivatives having a nitrous, hydroxylation or amino moiety in place of the moiety in eveminomicins B, C and D may be obtained by reduction of the nitro moiety in eveminomicins B, C and D in accordance with the procedures of U.S. Pat. No. 4,006,225. A preferred everninomicin is N-acetylaminoeveminomicin-D and is represented by Formula II wherein X=NHCOCH$_3$, Y=H; R$_4$=CH(OCH$_3$) (CH$_3$); R$_3$=R$_5$=H and R$_2$=CH$_3$. N-acetylaminoeveminomicin D and its di N-methylglucamine salt may be prepared by the procedures of U.S. Pat. No. 4,129,720 which discloses reduction of the nitro moiety of eveminomicins B, C and D to produce the amino derivatives which are subsequently converted into the N-acyl e.g. N-acetyl, N-alkyl, e.g. NH(C$_2$H$_5$), or N,N-dialkyl, e.g. N(C$_2$H$_5$)$_2$, derivatives. The preparation of the N-acyl-N-hydroxylamino eveminomicin B, C and D derivatives and pharmaceutically acceptable salts thereof are also described. The preparation of Eveminomicin 7 represented by Formula II wherein X=OH, Y=H, R$_4$=CH(OCH$_3$) (CH$_3$), R$_5$=H and R$_2$=CH$_3$ is disclosed by A. K. Ganguly et al. in *J. Chem. Soc. Chem. Comm.* 1980, 56–58.

The "eveminomicin-type" antibiotics are those lipophilic oligosaccharide antibiotics represented by Formula II wherein X=NO$_2$, NO NH$_2$, OH, NHCOCH$_3$, NHC$_2$H$_5$, N(C$_2$H$_5$)$_2$, NHOH or H, Y=OH, R$_2$=CH$_3$ or H; R$_3$=H, R$_4$=CH(OCH$_3$)(CH$_3$) or H and

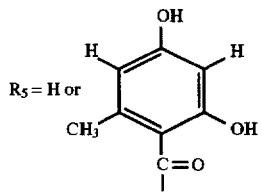

The compounds of Formula II wherein X=NO$_2$ or NH$_2$, Y=OH

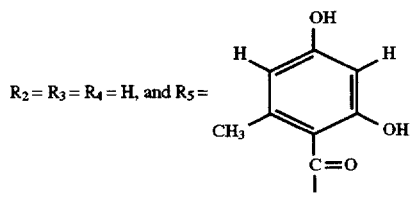

are isolated from an antibiotic 13–384 complex produced by fermentation of the organism *Micromonospora carbonacea* var. africana, NRRL 15099, ATCC 39149. Antibiotic components 1 (Formula II, X=NO$_2$ and Y, R$_2$, R$_3$, R$_4$ and R$_5$ are each defined as hereinabove in reference to antibiotic 13–384) and 5 (Formula II, X=NH$_2$ and Y, R$_2$, R$_3$, R4, and R$_5$ are as defined as hereinabove in reference to antibiotic 13–384) disclosed in U.S. Pat. Nos. 4,597,968 and 4,735,903 have the structural Formulas disclosed by A. K. Ganguly et al. in *Heterocycles* (1984) vol. 28 (No.1) pp. 83–88. The eveminomicin-type antibiotics of Formula II wherein X=H, NHOH, NHCOCH$_3$ and acyl and alkyl derivatives thereof are described in U.S. Pat. Nos. 4,622,314 and 4,767,748.

The preferred compositions of matter of this invention include compounds of Formula II wherein R$_3$=H.

| and X | Y | R$_4$ | R$_5$ | R$_2$ |
|---|---|---|---|---|
| NO$_2$ | OH | CH(OCH$_3$)(CH$_3$) | H | CH$_3$ |
| OH | H | " | " | " |
| NO$_2$ | H | H | " | " |
| NO$_2$ | H | CH(OCH$_3$)(CH$_3$) | " | " |
| NHCOCH$_3$ | H | " | " | " |
| NO$_2$ | OH | H | 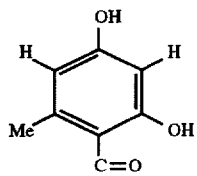 | H |
| H | " | " | " | " |
| NHOH | " | " | " | " |
| NHCOCH$_3$ | " | " | " | " |
| NH$_2$ | " | " | " | " |
| NHC$_2$H$_5$ | " | " | " | " |
| N(C$_2$H$_5$)$_2$ | " | " | " | " |

The most preferred eveminomicin-type antibiotic is named 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) having the molecular Formula of: C$_{70}$H$_{97}$NO$_{38}$Cl$_2$ and the molecular weight of 1629 and is represented by Formula III.

The preferred compound of the Formula III may be obtained by fermentation of *Micromonospora carbonacea* var. africana NRRL 15099, ATCC 39149 or, more preferably, by an improved strain thereof, obtained as hereinafter described.

Utilizing the strain SCC 1413 of the culture NRRL 15099, ATCC 39149, the preferred compound of the Formula III may suitably be obtained by the procedures outlined in Example I of U.S. Pat. No. 4,597,968. In a specific example, in accordance with this procedure, the initial stage inoculum for the fermentation of strain SCC 1413 was prepared by transferring 2.5 ml of a frozen whole broth of 50 ml of the germination medium in 250 ml Erlenmeyer flasks. The germination medium consisted of beef extract, 0.3%; tryptone, 0.5%;dextrose, 0.1%; potato starch, 2.4%; yeast extract, 0.5%; and calcium carbonate, 0.2%. The pH of the medium was adjusted to 7.5 prior to sterilization. The flasks were incubated at 30° C. on a gyratory shaker at 300 rpm for 48 hours. For the second stage germination, 2 liter Erlenmeyer flasks containing 350 ml of the same medium were inoculated with a 5% volume of the first stage germination. The conditions for incubation were the same as before. A third inoculum stage was employed for all stirred tank fermentations and was prepared by a 24 hour incubation of the culture under the same conditions as employed for the second stage.

Ten liter fermentations were initially carried out in 14 liter NBS Laboratory Fermentors in a fermentation medium containing yeast extract, 0.5%; casein hydrolysate, 0.5%; cerelose, 1%; soluble starch, 2.0%; calcium carbonate, 0.4%; and cobalt chloride, 0.24 mg %. The pH of the medium was adjusted to 6.7 before sterilization and to 7.0 before inoculation. The third stage inoculum (2.5%) was used to initiate the fermentation which was conducted at 30° C. with 0.35 vvm of air and 350 rpm agitation.

During the course of the fermentation, antibiotic production was monitored every 24 hours by bioassay of the whole broth against *Staphylococus aureus* 209P (pH of the agar, 7.0) and *Escherichia coli* ATCC 10536 (pH of the agar, 8.0). The growth of the producing organism (packed cell volume), pH and dissolved oxygen levels were also determined either intermittantly or continuously.

The course of a typical 10 liter tank fermentation is illustrated in FIG. 1.

We have developed an improved strain from SCC1413, NRRL 15099, ATCC 39149 using standard mutagenesis agents and obtained strains producing improved yields of the preferred eveminomicin-type antibiotic compound of the Formula III. In a specific example, the parent strain SCC 1413, NRRL 15099, ATCC 39149 was exposed to an amount of the mutagenesis agent, N-nitrosoguanidine (NTG) sufficient to kill 90% of a culture of SCC 1413, ATCC 39149, NRRL 15099. Fifteen hundred surviving isolates were examined for enhanced biological activity against *S. aureus* and *E. coli* to determine which isolates exhibited improved production of the desired antibiotic of Formula III. The test procedure employed to determine enhanced activity was as follows: Single colony isolates were germinated in test tubes containing 10 ml of germination media of Example 1 of U.S. Pat. No. 4,597,968 and shaken at 250 rpm on a gyratory shaker at 30° C. for 48 hours. Fermentation studies were initiated by transferring 2.5 ml of the seed to 250 ml Erlenmeyer flasks containing 50 ml of fermentation media and incubating at 30° C. for 96 hours at 250 rpm on a gyratory shaker. The antibiotic obtained following fermentation was then assayed for improved antibiotic production by assessing the activity against *S. aureus*. and *E. coli* and isolates giving improved yields of the desired antibiotic were identified. The results for a representative improved isolate, designated herein as strain SCC 1631, are given in Table 5.

The foregoing strain-development procedure was repeated by subjecting the representative improved isolate, SCC 1631, to a further exposure to NTG, again in an amount sufficient to kill 90% of the cultures, followed by selection of the isolates on agar plates containing 150 µg/mL of eveminomicin D. Isolates giving enhanced production of the desired antibiotic were again selected by assessing biological activity thereof against *S. aureus* and *E. coli*. One such isolate, herein designated strain SCC 1756, was then utilized to produce the preferred antibiotic of Formula III.

Further, NTG mutagenesis of SCC 1756 yielded our current production strain, SCC 2146.

In the foregoing mutation procedures, the protocols for both studies were as previously described hereinabove. For the latter two mutation studies, fermentation broths were extracted with ethyl acetate and the concentrates were chromatographed on Whatman LKGDF thin layer plates in a solvent system consisting of chloroform:methanol (9:1 v/v) followed by bioautography against *S. aureus* and *E. coli* to confirm the production of all components of the antibiotic complex. To follow increased titers of the compound of Formula III, thin layer plates were examined by using the Shimadzu CS-930 TLC plate scanner and quantitating the higher producing extracts by using HPLC. Combined titers are defined as the sum of the compound of Formula III (antibiotic 13-384, component 1 of USP 4,597,968) and the nitroso analog of said component 1, i.e., antibiotic 13-384, component 1a.

Early observations indicated that although the parent strain SCC 1413 grew rapidly at 34° C., antibiotic production was optimal if the temperature was lower. This phenomenon was investigated as a means of fermentation optimization. Results of the temperature study indicated that optimal production was obtained when the temperature was lowered from 34° C. to 30° C. after 24 hours of incubation. All subsequent work in stirred tanks followed the protocol of incubating the fermentation at 34° C. for 24 hours followed by lowering the temperature to 30° C. for the duration of the fermentation run.

Media studies were conducted in conjunction with the isolation of the improved production strains. Carbon and nitrogen source substitutions were investigated as well as the addition of minerals and other complex nutrients. Replacement of casein hydrolysate by either meat or fish peptone and substituting potato dextrin (PDP 650) for soluble starch enhanced antibiotic production using strains SCC 1413 and SCC 1631. Subsequent enhancements in the production of the compound of Formula III were observed with the addition of corn steep liquor and nickel (II) chloride in studies with strain SCC 1756. The current production fermentation media (4I+½ Ni) optimized for the compound of Formula III contains glucose, 2.2 weight %; PDP 650 dextrin, 4.0 weight %; yeast extract, 0.5 weight %; meat peptone, 0.6 weight %; corn steep liquor, 0.5% vol., nickel chloride, $2.5 \times 10^{-6}M$; and calcium carbonate, 0.4 weight %. The pH of the medium was adjusted to 6.7 before the addition of calcium carbonate. Table 6 shows a comparison of the titers for strains SCC 1413, SCC 1631, SCC 1756 and SCC 2146 obtained in shake flask studies (50 ml of the current production medium in 250 ml erlenmeyer flasks, at 300 C, for 96 hours, at 300 rpm). The marked titer improvement (15 fold over the original parent, SCC 1413) is clearly demonstrated. Titers of 555–750 µg/ml (sum of the compound of Formula III and the nitroso derivative thereof) have been achieved in 100 liter fermentations using the current production medium with our best production strain, SCC 2146 (Table 7).

TABLE 5

Comparison of Strains SCC 1413 and SCC 1631 in Fermentations Showing Zones of Inhibition (mm) on Agar Plates[1]

| Strain | *S. aureus* pH 7 | | *E. coli* pH 8 |
|---|---|---|---|
| SCC | Udil. | 1:20 | Undil. |
| | | TEST 1 | |
| 1631 | 28.7, 28.7 | 22.0 | 20, 17.5 |
| 1413 | 28.7, 28.7 | 19.0 | 12 H[3], 12 H[3] |
| | | TEST 2 | |
| 1631 | 28.1, 28.8 | 23.3, 23.1 | 14.8 C[2], 15.0 C[2] |
| 1413 | 23.8, 23.1 | 20.5, 19.8 | 12 H[3], 12 H[3] |

[1] Duplicate Determinations Where Appropriate
[2] Clear Zone
[3] Hazy Zone

TABLE 6

Flask Comparison of SCC's 1413, 1631, 1756 and 2146 Strains of *Micromonospora Carbonacea* var *africana* NRRL 15099, ATCC 39149 Titer of the compound of Formula III and Nitroso Analog (1A) Thereof (µg/ml)

| Culture | 1 (NO$_2$) | 1a (NO) | combined (1 +1a) |
|---|---|---|---|
| SCC 1413 | 5 | 3 | 8 |
| SCC 1631 | 14 | 4 | 18 |
| SCC 1756 | 17 | 16 | 33 |
| SCC 2146 | 39 | 85 | 124 |

TABLE 7

100 Liter Fermentations of SCC 2146
Titer of Formula III and the NO Analog (1A) Thereof (µg/ml)

| Media | 1 (NO₂)[1] | 1a (NO)[2] | combined (1 + 1a) |
|---|---|---|---|
| 4I | 105 | 315 | 420 |
| 4I | 135 | 170 | 305 |
| 4I + ½Ni[3] | 55 | 500 | 555 |
| 4I + Ni[4] | 150 | 575 | 725 |
| 4I + ½Ni[3] | 100 | 650 | 750 |
| 4I + ½Ni[3] | 130 | 470 | 600 |

Footnotes to Table 7
[1] The everninomicin-type antibiotic of Formula III.
[2] The Nitroso analog of the antibiotic of Formula III.
[3] Nickel concentration (½Ni) 2.5 × 10⁻⁶M.
[4] Nickel concentration Ni = 5 × 10⁻⁶M.

The isolation of the lipophilic oligosaccharide antibiotic complex containing the compound of Formula III and the nitroso analog thereof was accomplished by use of the procedures of Example 1C of U.S. Pat. No. 4,597,968. The fermentation broth was adjusted to pH 7 and extracted twice with a volume of ethyl acetate two times the volume of the fermentation broth. The combined ethyl acetate extracts were concentrated and the amounts of the compound of Formula III and the nitroso analog thereof were determined by HPLC. The nitroso analog was converted into the nitro compound of Formula III by use of an oxidizing agent such as tertiary butyl hydroperoxide (t-BuO₂H) with vanadyl acetylacetonate dissolved in an aprotic organic solvent at room temperature. The course of the reaction was monitored by, for example, HPLC. The reaction mixture was quenched with trialkylphosphite and the crude product was purified by standard chromatographic techniques. e.g. silica gel column chromatography (acetone/CH₂Cl₂) or a column containing a polyhydroxyvinyl polymer such as Fractogel (Toyo Pearl) available from Toyo Haas, Philadelphia, Pa.

The pharmaceutically acceptable composition of matter of this invention may contain, in addition to (a) an antibiotic of Formula I, II, III, (b) at least a stoichiometric amount of a base capable of forming a pharmaceutically acceptable salt of such antibiotics and (c) an specified amount of a binding agent, preferably recombinant human albumin, and (d) 0 weight percent (basis total weight of the composition) to about an iso-osmotic amount of a pharmaceutically acceptable tonicity agent and pharmaceutically acceptable carriers. The preferred pharmaceutically acceptable carriers include sterile water for injection and others that produce pharmaceutically acceptable compositions. i.e., compositions which when dissolved in a pharmaceutically acceptable carrier are substantially free of visible particles.

BIOLOGICAL ACTIVITIES

We have surprisingly found that the preferred composition of matter of this invention, comprising one mole of the compound represented by Formula III, 3 moles of NMG and 0.027 moles of human serum albumin, has substantially the same geometric mean MICs (GMM) against various bacteria, and substantially the same serum protein binding values as the compound of Formula III per se. It is expected that all the compositions of matter of this invention will behave similarly.

The in vitro antibacterial activity tests were performed via conventional agar dilution methods in Mueller-Hinton agar. The GMMs for the above-listed preferred composition of matter of this invention and for the compound of Formula III were determined against various bacteria, e.g., gram positive and gram negative bacteria. The term "susceptible gram positive and gram negative bacterial infections" means a broad range of gram positive bacterial infections, e.g., methicillin-resistant and methicillin-susceptible staphylococci, various strains of streptococci and enterococci and some gram negative bacterial infections, e.g., Moraxella, Haemophiluf and Legionella. The compound of Formula III had excellent activity (2-fold more potent than vancomycin) against both methicillin - resistant staphylococci (GMM, 0.1 µg/ml) and methicillin - susceptible staphylococci (GMM, 0.5 µg/ml). The compound of Formula III also had good activity (similar to that of vancomycin) against Enterococcus faecalis and Enterococcus faecium (GMM, 0.49 µg/ml) and similarily good activity against enterococci resistant to vancomycin (MICs,>128 µ/ml) and good activity (MICs,<0.5 µg/ml) against various strains of streptococci. The compound of Formula III was very active against Borrelia burgdorferi (MICs,<0.49 µg/ml) and Legionella pneumophila and L. longbeacheae (MICs 2.5 µg/ml) but was only slightly active against gram-negative bacteria (GMM,>760 µg/ml), Trichomonas vaginalis (MICs, >192 µg/ml) and Mycoplasma sp. (MICs 200 µg/ml). No cross resistance with other antibiotics was observed.

The compound of Formula III had moderate bactericidal activity against various clinical and laboratory strains of staphylococci. The bactericidal activity of the compound of Formula III against staphylococci and enterococci was similar to that of vancomycin. The compound of Formula III had good activity against staphylococci in mice (PD₅₀range 0.5 to 25.0 mg/kg), similar to that of vancomycin (0.7 to 28.5 mg/kg).

Following IV administration (30 mg/kg) of the compound of Formula III and 2 molecules of NMG, high serum levels were seen in rats (peak about 90 ug/ml) with a long serum beta half life.

The pharmaceutically acceptable compositions of matter of this invention are expected to be active against the above-listed susceptible bacteria as well as against spirochetes including Treponema pallidum, anaerobes including Clostridium difficile as well as against Pneumocystis, Toxoplasma, protozoa and helminths.

Based on the activity of the compound of Formula III against Borrelia burgdorferi, Legionella pneumophila and L. longbeacheae, we expect that the compositions of matter containing the compound of Formula III will exhibit activity in humans against Lyme disease and legionaire's disease.

The present invention provides a method of treating or preventing susceptible gram-positive and gram-negative bacterial infections in animals by administering to such animals especially man afflicted with such infections an amount or a pharmaceutical composition of the compositions of matter of this invention and a pharmaceutically acceptable carrier therefor.

The compositions of matter of this invention may be combined with any pharmaceutically acceptable carrier, e.g., non-ionic surfactants, sterilized water, aqueous ethanol, vegetable oils, or polyols, e.g., polyethylene glycols and propylene glycol and administered orally, parenterally or topically in a variety of formulations. The use of sterile water for injection as a carrier is preferred. The sterile water for injection may optionally contain pharmaceutically acceptable substances, e.g. sodium chloride, potassium nitrate, glucose, mannitol, dextrose, sorbitol, xylitol or buffers such as phosphate, acetate or citrate as well as preservatives.

The compositions of matter of this invention are prepared by admixing a lipophilic oligosaccharide antibiotic of Formula I, II or III with at least about a stoichiometric amount of a base capable of forming a pharmaceutically acceptable salt thereof in a suitable solvent such as water and with a specified amount of a binding agent, for example human serum albumin. The order of admixing is not critical, but preferably an aqueous solution of the specific binding agent is admixed with the base or alternatively it may be added after the base is admixed with the lipophilic oligosaccharide antibiotic and a tonicity agent such as mannitol. The formation of the aqueous solutions may take place at a temperature between 20° and 25° C. The aqueous solution so formed is filtered to produce a clear aqueous solution of the complex which may be evaporated or preferably freeze-dried to form the compositions of matter of this invention in the form of a lyophilized powder which is readily reconstituted by addition of an amount of a pharmaceutically acceptable carrier such as sterile water for injection. The pharmaceutically acceptable non-ionic surfactant e.g. polysorbate-80, when used, would be added to the aqueous solution before filtration and lyophilization. Alternatively, the aqueous solution may be frozen, thawed and thereafter filtered before use, e.g., as an intravenous IV formulation. It is a special feature of the present invention that the pharmaceutical compositions of the present invention form aqueous solutions and yet contain about 0.006 to about 0.03 mole, preferably about 0.027 mole of human serum albumin per mole of a compound of formula 1, 11 or III. The discovery that pharmaceutical compositions useful for safely and effectively delivering lipophilic oligosaccharide antibiotics to the serum of animals afflicted with susceptible bacterial infections, especially susceptible gram positive and gram negative bacterial infections, could be prepared by use of such a small amount of human serum albumin is particularly unexpected.

It is believed that even 0.006 moles of recombinant human serum albumin per mole of compound of formula 1, II or IIII (substantially free of fatty acids and other impurities) will also be effective in the compositions of the present invention.

For oral administration, the compositions of this invention may be compounded in the form of tablets, capsules, elixers or the like. Tablets and capsules may contain such excipients as starch or lactose; liquid forms may contain coloring or flavoring agents. Topical preparations may be in the form of creams, hydrophobic and hydrophilic ointments, or aqueous, non-aqueous or emulsion-type lotions as well as pessaries or powders. Typical carriers for such formulations are water, oils, greases, polyesters and polyols. Parenteral formulations, e.g., injectable dosage forms, are usually liquids such as solutions or suspensions, with typical carriers being sterile water, saline solution and 5% by weight dextrose solutions. Parenteral formulations are preferred. Intravenous (IV) formulations are more preferred.

The dose to be administered in any particular dosage form will depend upon various factors, such as the weight, age and sex of the animal especially a mammal such as a human being being treated, the susceptibility of the infecting organism to the lipophilic oligosaccharide antibiotic, the stage and severity of the infection. Generally, the dosage of the lipophilic oligosaccharide antibiotics of Formula I, II or III administered is from about 1.0 mg to about 15 mg per kilogram of body weight, preferably about 3–5 mg per kilogram of body weight per day in divided dosages. The specified dosage is left to the discretion of the practitioner who will take into consideration the age and sex of the patient as well as, inter alia, the severity of the infection to be treated. IV administration is preferred.

In treating certain patients with the compositions of this invention, it is possible to include other pharmaceutically active ingredients in the same dosage unit.

EXAMPLES

Example 1

A 100 liter fermentation of strain SCC 2146 of *Micromonospora carbonacea* var. africana NRRL 15099, ATCC 39149 improved as described hereinabove, was conducted in accordance with the procedures of Example 1 B of U.S. Pat. No. 4,597,968 except that the following production medium (41+½× Ni) was used and that the fermentation was conducted at 34° C. for 24 hr followed by lowering the temperature to 30° C. for the duration of the fermentation run, i.e., for another 72 hr (total fermentation time of 96 hr). Aeration and agitation rates were, 0.35 vvm and 350 rpm, respectively

| Glucose | 2.2% (weight) |
| --- | --- |
| PDP 650 dextrin | 4.0% (weight) |
| Yeast Extract | 0.5% (weight) |
| Meat Peptone | 0.6% (weight) |
| Corn Steep Liquor | 0.5% (volume) |
| Nickel Chloride | $2.5 \times 10^{-6}$M |
| Calcium Carbonate | 0.4% (by weight) |
| Tap Water q.s. to give | 1000 ml |

Extract the fermentation broth of Example 1 A twice with 200 L of ethyl acetate. Combine the ethyl acetate extracts and concentrate to provide a concentrated antibiotic complex containing a mixture of the compound of Formula III and the nitroso analog thereof (as determined by HPLC).

Example 2

A) To 919 g of antibiotic complex produced as described in Example I and containing 294 g (32%) of a mixture of 3.4 moles of the nitroso analog to one mole of the compound of Formula III dissolved in 4.6 L of ethyl acetate, 68.8 g of $NaHCO_3$ and 2.98 g of vanadyl acetylacetonate 3M in 2,2,4-trimethylpentane available from Aldrich (0.06 eq); 394 mL of 3M t-butylhydroperoxide was added to the so-formed mixture after a ½ hour period. Portions of 1.45g (0.03 eq) of vanadyl acetylacetonate were added thereto at 0 and after 1½, 2½, 3½ and 4 hours so that 0.15 eq of vanadyl acetylacetonate was added over 4 hours. The reaction mixture was immersed in an ice bath, and 203 mL (0.5 eg) of triethylphosphite $(C_2H_5O)_3P$ was added thereto. The so-formed reaction mixture was diluted with an equal amount of ethyl acetate while keeping the temperature of the reaction mixture at <30° C. The diluted ethyl acetate reaction mixture was washed twice with water. The aqueous layers were salted and extracted with ethyl acetate. The combined organic extracts were dried over $MgSO_4$, filtered and concentrated. The so-formed residue was dissolved in a minimum amount of acetone and precipitated into 7 L of 1:9 (v/v) ethyl ether/hexane. The residue was filtered and washed with hexane dried under vacuum and heat to give 928 g containing 30% (278 g) of the nitro compound of Formula III.

B) The residue of Example 2A was purified on 5 kg of silica gel in a column. The column was eluted with 12 liters of $CH_2Cl_2$ containing successively 10%, 20%, 25%, 30%, 35% (v/v) of acetone. The appropriate fractions were combined and concentrated at <35° C. The so-formed residue was dissolved in acetone and precipitated into 10 parts of 10% ethyl ether/hexane. The product was filtered and dried under vacuum without heat. The main fraction contained 147.5 g of the compound of Formula III (98.7% pure). The other fractions contained crude product and were subjected to repeated silica gel chromatography until at least a 96–98% pure product was obtained. The structure was determined by NMR and MS and found to be consistent with that of Formula III.

Example 3

An aqueous solution containing 58.3 g of manitol (USP and EP) and 42.0 g of N-methyl glucamine ("NMG") USP and BP was prepared in 2.0 L of water.

To this solution was added 117g of the compound of Formula III followed by addition of 555 g of 25% by weight HSA solution (Armour Pharmaceuticals). The so-formed solution was brought to a final volume of 2.9 L. After agitation, a homogeneous solution containing 40 mg per mL of the compound of Formula III was formed. The molar ratios of the three components were 1 mole of the compound of Formula III to 3 moles of "NMG" to 0.027 moles of HSA. The so-formed solution was filtered, filled into vials and freeze-dried to form a powder. For reconstitution of the powder to form a pharmaceutical composition, a pharmaceutically acceptable carrier such as sterile water for injection USP was added to the freeze-dried powder.

The safe and effective administration of the pharmaceutical composition of clear aqueous solutions of the homogeneous complex prepared in accordance with the procedures of this invention was tested in various in-vivo animal models by reconstituting the lyophilized powder with sterile water for injection to give solution containing 80 mg/mL of the compound of formula III such are reported in Tables 1 and 4.

A similar procedure may be used to prepare pharmaceutical compositions containing recombinant human albumin ("rHA") by replacing HSA with an equivalent amount of rHA.

Example 4

A 100-mL aqueous solution containing 160 mg/mL of compound of Formula III and 57.6 mg/mL of NMG was prepared as a stock solution. To each 10 mL of this solution was added 1.6, 3.2, 4.8, 6.4 and 8.0 mL of 25% human serum albumin solution and sterile water for injection was added to the so-formed solution to provide a solutions with a final volume of 20 mL containing 80 mgmL of the compound of Formula III. The molar ratio of the three components were 1 mole-of the compound of Formula III to 3 moles of NMG to 0.006, 0.012, 0.018, 0.024 and 0.03 moles of HSA. The solutions so formed were filtered and used for animal testing.

Example 5

This example provides the preparation of the composition used for the studies in rats and mice summarized in Table 1. The procedure of Example 3 was followed using the following ingredients in the listed amounts:

| Ingredients | mg/Vial | % W/W[1] |
|---|---|---|
| Compound of formula III | 200 | 33.5 |
| NMG US and BP | 72 | 12.1 |
| HSA USP and EP | 225 | 37.7 |
| Mannitol USP, BP and EP | 100 | 16.7 |
| Water for injection USP | sublimed | — |

1) The weight of each ingredient to the total weight of all ingredients.

The molar ratio of III:NMG:HSA was 1:3:0.027

The reconsituted solution was not iso-osmotic but use of a total of 200 or 300 mg of mannitol (instead of only 100 mg as used above) would likely render the solution iso-osmotic.

Example 6

This example illustrates preparation of a composition such as used in Table 2 and containing 2 to 10% WN based of a solution containing 80 mg/mL of the compound of formula III. The procedure of Examples 4 and 5 were followed to prepare a solution containing the compound of formula III, NMG and HSA in the molar ratio of 1:3: 0.006 to 0.03.

| Human serum albumin (HSA) | Broad Range Studied |
|---|---|
| mg HSA per 200 mg of compound of formula III | 50–250 |
| moles per one mole of III | 0.006–0.03 |
| mg/mL per 80 mg/mL of III | 20–100 |
| % w/v/ based on 80 mg/mL of the solution containing III | 2–10% |

Example 7

This example provides compositions which may be prepared in accordance with the procedures of example 4 having a range of ingredients in compositions shown below.

| Ingredient | Broad Range Mg/200 mg. of III | Relative Molar Ratio based on one mole of III |
|---|---|---|
| Compound of Formula III | 200 | 1 |
| NMG, USP and BP | 48–144 | 2–6 |
| HSA, USP and EP | 50–250 | 0.006–0.03 |
| Mannitol, USP, BP and EP | 200–400 | 9.0–18 |
| Sterile Water for injection USP | sublined | |

| Ingredient | Preferred Range Mg/200 mg. of III | Molar Ratio based on one mole of III |
|---|---|---|
| Compound of Formula III | 200 | 1 |
| NMG, USP and BP | 72–84 | 3–3.5 |
| HSA, USP and EP | 150–250 | .018–.03 |
| Mannitol, USP, BP and EP | 200–300 | 9.0–13.5 |
| Sterile Water for Injection, USP | sublim,ed | |

What is claimed is:

1. A composition of matter comprising:

(a) a lipophilic oligosaccharide antibiotic represented by Formula I;

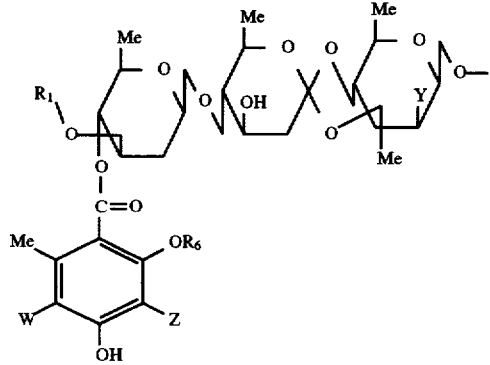

wherein

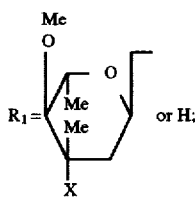

X is one of $NO_2$, NO, $NH_2$, $NHCOCH_3$, NHOH, $NH(C_2H_5)$, $N(C_2H_5)_2$, OH or H;

$R_2$ is one of $CH_3$, $COCH(CH_3)_2$, $COCH_3$, $CO(CH_2)_3CH_3$, $COCH_2CH_3$ or H;

$R_3$ is one of $CH_3$ or H;

$R_4$ is one of $COCH_3$, $CH(OCH_3)(CH_3)$, $CH(OH)CH_3$, CHO, or H;

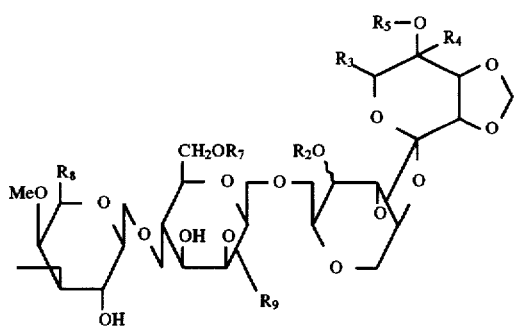

$R_5$ is one of

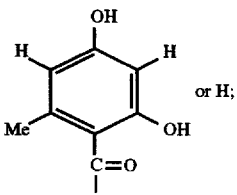

$R_6$ is $CH_3$ or H;
$R_7$ is $CH_3$ or H;
$R_8$ is $CH_3$, $CH_2OH$ or H
$R_9$ is $CH_3$ or H;
Y is OH, $CH_3$, or H;
W is Cl or H; and
Z is Cl or H;

(b) at least about a stoichiometric amount of a base capable of forming a pharmaceutically acceptable salt with a lipophilic oligosaccharide antibiotic of Formula I;

(c) an amount of binding agent sufficient to achieve efficacious delivery of said lipophilic oligosaccharide antibiotic to the serum of an animal while simultaneously avoiding adverse reaction syndrome; and (d) 0% by weight (basis, total weight in said composition) up to an iso-osmotic amount of a pharmaceutically acceptable tonicity agent.

2. The composition of claim 1 wherein the lipophilic oligosaccharide antibiotics represented by Formula 1 are selected from the group consisting of flambamycin, the everninomicins, the everninomicin-type antibiotics, curamycin, and the avilamycin A-N antibiotics.

3. The composition of claim 1 wherein he base is selected from the group consisting of chloroprocaine, procaine, piperazine, glucamine, N-methylglucamine, N'N-dimethylglucamine, ethylenediamine, diethanolamine, diisopropylamine, diethylamine, N-benzyl-2-phenylethylamine, N,N'-dibenzylethylenediamine, choline, clemizole, tris(hydroxymethyl)aminomethane, D-glucosamine and sodium hydroxide.

4. The composition of claim 1 wherein the base is N-methylglucamine.

5. The composition of claim 1 wherein the binding agent is HSA.

6. The composition of claim 1 wherein the binding agent is rHA.

7. A composition of matter comprising:

(a) a lipophilic oligosaccharide antibiotic represented by the Formula II

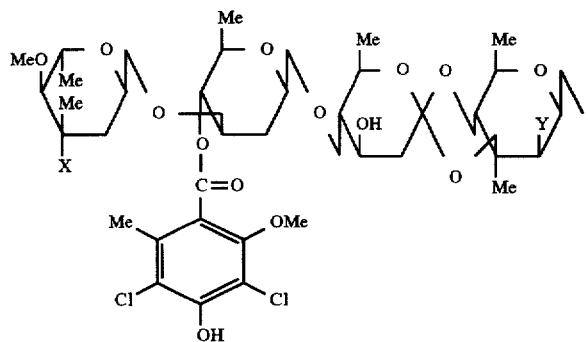
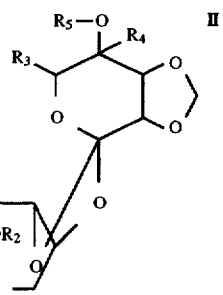

wherein X is one of $NO_2$, NO, NHOH, $NH_2$, $NHCOCH_3$, $NHC_2H_5$, $N(C_2H_5)_2$, OH or H Y is OH or H $R_2$ is H or $CH_3$ $R_3$ is H $R_4$ is H or $CH(OCH_3)(CH_3)$ and

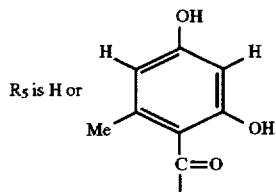

$R_5$ is H or (b) at least about a stoichiometric amount of a base capable of forming a pharmaceutically acceptable salt with a lipophilic oligosaccharide antibiotic of Formula II;

(c) an amount of a binding agent sufficient to achieve efficacious delivery of said lipophilic oligosaccharide antibiotic to the serum of an animal while simultaneously avoiding occurrence of adverse reaction syndrome; and (d) 0% by weight (basis, total weight of said composition) up to an iso-osmotic amount of a pharmaceutically acceptable tonicity agent.

8. The composition of claim 7 wherein the base is selected from the group consisting of chloroprocaine, procaine, piperazine, glucamine, N-methylglucamine, N'N-dimethylglucamine, ethylenediamine, diethanolamine, disopropylamine, diethylamine, N-benzyl-2-phenylethylamine, N,N'-dibenzylethylenediamine, choline, clemizole, tris(hydroxymethyl)aminomethane, D-glucosamine and sodium hydroxide.

9. The composition of claim 7 wherein the base is N-methylglucamine.

10. The composition of claim 7 wherein the biding agent is HSA.

11. The composition of claim 7 wherein the binding agent is rHA.

12. A composition of matter comprising:

(a) the lipophilic oligosaccharide antibiotic represented by Formula III

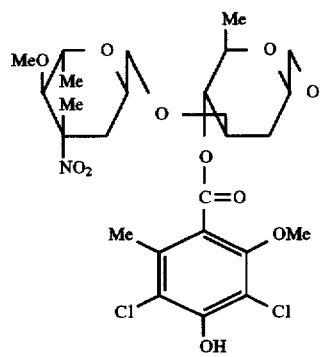
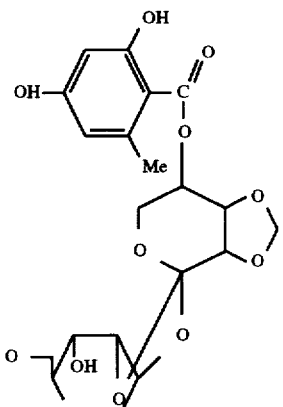

(b) at least about two equivalents of a base (per mole of the compound of Formula III) capable of forming a pharmaceutically acceptable salt of said lipophilic oligosaccharide antibiotic of Formula III (c) an amount of a binding agent sufficient to achieve efficacious delivery of said lipophilic oligosaccharide antibiotic to the serum of an animal while simultaneously avoiding occurrence of adverse reaction syndrome; and (d) 0% by weight (basis, total weight of said composition) of up to an iso-osmotic amount a pharmaceutically acceptable tonicity agent.

13. The composition of claim 12 wherein the base is selected from the group consisting of chloroprocaine, procaine, piperazine, glucamine, N-methylglucamine, N'N-dimethylglucamine, ethylenediamine, diethanolamine, diisopropylamine, diethylamine, N-benzyl-2-phenylethylamine, N,N'-dibenzylethylenediamine, choline, clemizole, tris(hydroxymethyl)aminomethane, D-glucosamine and sodium hydroxide.

14. The composition of claim 12 wherein the base is N-methylglucamine.

15. The composition of claim 12 wherein a tonicity agent is present.

16. The composition of claim 15 wherein the tonicity agent is mannitol.

17. The composition of claim 12 wherein the mole ratio of (a):(b):(c) is 1 :about 2–6:about 0.006 to 0.030.

18. The composition of claim 12 wherein the binding agent is HSA.

19. The composition of claim 12 wherein the binding agent is rHA.

20. A composition of matter comprising (a) the lipophilic oligosaccharide antibiotic represented by Formula III.

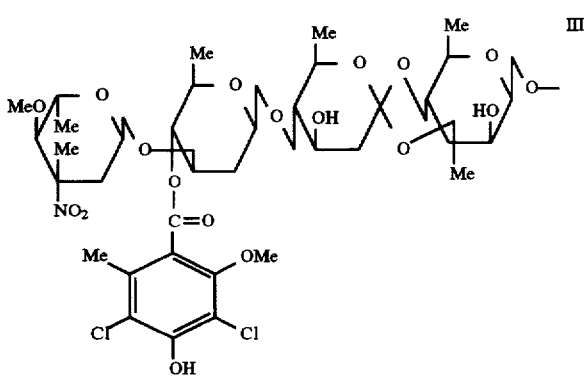

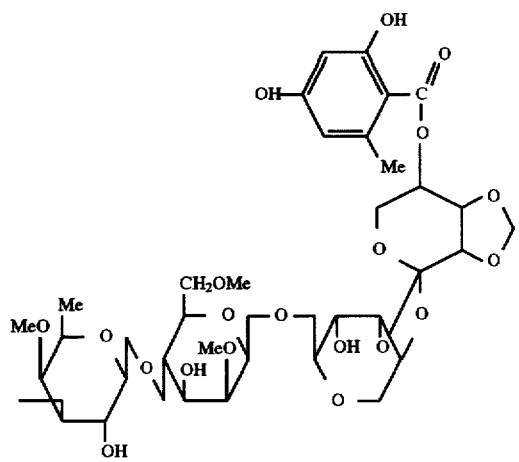

(b) at least about two equivalents of a base (per mole of said antibiotic of Formula III) capable of forming a pharmaceutically acceptable salt of said antibiotic of Formula III (c) an amount of recombinant human albumin sufficient to achieve efficacious delivery of said lipophilic oligosaccharide antibiotic to the serum of an animal while simultaneously avoiding occurrence of adverse reaction syndrome; and (d) an iso-osmotic amount of mannitol as a tonicity agent.

21. The composition of claim 20 wherein the base is N-methylglucamine.

22. The composition of claim 20 wherein the iso-osmotic amount of mannitol is 35 to 45% by weight of total composition.

23. The composition of claim 20 wherein the molar ratio of (a):(b):(c) is 1 :about 3–3.5: about 0.018 to 0.030.

24. The composition of claim 20 wherein the binding agent is HSA.

25. The composition of claim 20 whereas the binding agent is rHA.

26. A pharmaceutical composition for treating susceptible gram-positive and/or gram-negative bacterial infections comprising an antiinfective amount of a composition of matter of claim 20 and a pharmaceutically acceptable carrier thereof.

27. A method for treating susceptible gram-positive and/or gram-negative baceterial infections comprising administering to a mammal in need of such treating an antiinfective amount of a composition of matter of claim 20 or said composition of matter in combination with a pharmaceutically acceptable carrier.

* * * * *